(12) United States Patent
Sakaguchi et al.

(10) Patent No.: US 10,169,845 B2
(45) Date of Patent: Jan. 1, 2019

(54) MEDICAL IMAGE PROCESSING APPARATUS, X-RAY DIAGNOSTIC APPARATUS, PHANTOM, AND MEDICAL IMAGE PROCESSING METHOD

(71) Applicants: Toshiba Medical Systems Corporation, Otawara-shi (JP); Fujita Health University, Toyoake-shi (JP)

(72) Inventors: Takuya Sakaguchi, Utsunomiya (JP); Takashi Ichihara, Nagoya (JP)

(73) Assignees: Toshiba Medical Systems Corporation, Otawara-shi (JP); Fujita Health University, Toyoake-shi (JP)

( * ) Notice: Subject to any disclaimer, the term of this patent is extended or adjusted under 35 U.S.C. 154(b) by 0 days.

(21) Appl. No.: 14/574,614

(22) Filed: Dec. 18, 2014

(65) Prior Publication Data
US 2015/0178916 A1 Jun. 25, 2015

(30) Foreign Application Priority Data

Dec. 25, 2013 (JP) ................................ 2013-268127

(51) Int. Cl.
G06K 9/00 (2006.01)
G06T 5/00 (2006.01)
A61B 6/00 (2006.01)

(52) U.S. Cl.
CPC ............... *G06T 5/00* (2013.01); *A61B 6/481* (2013.01); *A61B 6/5205* (2013.01);
(Continued)

(58) Field of Classification Search
None
See application file for complete search history.

(56) References Cited

U.S. PATENT DOCUMENTS 4,124,799 A 11/1978 Schittenhelm
4,352,020 A * 9/1982 Horiba .................. A61B 6/583
250/252.1

(Continued)

FOREIGN PATENT DOCUMENTS

JP 55-075304 5/1980
JP 10-262959 10/1998
(Continued)

OTHER PUBLICATIONS

Jingwu Yao et al. "Linear Quantification Correction for Myocardial Perfusion Imaging from X-Ray Coronary Angiography", 2012 IEEE Nuclear Science Symposium and Medical Imaging Conference Record (NSS/MIC), 2012, 6 pages.

(Continued)

*Primary Examiner* — Avinash Yentrapati
(74) *Attorney, Agent, or Firm* — Oblon, McClelland, Maier & Neustadt, L.L.P.

(57) ABSTRACT

According to one embodiment, a medical image processing apparatus includes an image acquisition part and a data processing part. The image acquisition part is configured to obtain X-ray image data of an object including not less than three phantoms whose X-ray absorption factors are different from each other. The data processing part is configured to generate corrected X-ray image data of the object by correcting the obtained X-ray image data or other X-ray image data. The obtained X-ray image data or the other X-ray image data are corrected using a nonlinear function obtained based on pixel values of the obtained X-ray image data. The pixel values correspond to the phantoms.

12 Claims, 10 Drawing Sheets

(52) U.S. Cl.
CPC ............ *A61B 6/5258* (2013.01); *A61B 6/583* (2013.01); *G06T 5/007* (2013.01); *A61B 6/504* (2013.01); *G06T 2207/10116* (2013.01)

(56) References Cited

U.S. PATENT DOCUMENTS

| | | | |
|---|---|---|---|
| 4,400,827 A | 8/1983 | Spears | |
| 4,782,502 A * | 11/1988 | Schulz | A61B 6/032 250/252.1 |
| 5,222,021 A * | 6/1993 | Feldman | A61B 6/583 378/18 |
| 5,615,279 A * | 3/1997 | Yoshioka | G06T 11/005 378/7 |
| 6,990,222 B2 * | 1/2006 | Arnold | A61B 5/02007 378/18 |
| 7,496,175 B2 | 2/2009 | Sakaguchi et al. | |
| 8,186,880 B1 * | 5/2012 | Arnold | A61B 6/032 378/18 |
| 8,818,058 B2 * | 8/2014 | Paul | A61B 6/032 382/100 |
| 8,824,627 B2 * | 9/2014 | Nakanishi | G06T 11/005 378/19 |
| 8,867,814 B2 * | 10/2014 | Lonn | G06T 11/005 382/128 |
| 9,392,991 B2 | 7/2016 | Chide et al. | |
| 2004/0228451 A1 * | 11/2004 | Wu | A61B 6/583 378/207 |
| 2007/0100226 A1 * | 5/2007 | Yankelevitz | A61B 5/1075 600/407 |
| 2007/0172025 A1 * | 7/2007 | Seto | A61B 6/541 378/18 |
| 2008/0167552 A1 * | 7/2008 | Bouchevreau | A61B 6/481 600/431 |
| 2008/0212859 A1 * | 9/2008 | Da Silva | A61B 6/12 382/131 |
| 2008/0273782 A1 * | 11/2008 | Ichihara | A61B 5/0275 382/131 |
| 2008/0287787 A1 * | 11/2008 | Sauer | A61B 8/12 600/437 |
| 2010/0278409 A1 * | 11/2010 | Wiemker | A61B 6/583 382/131 |
| 2010/0315087 A1 * | 12/2010 | Thulborn | G01R 33/3415 324/318 |
| 2011/0129057 A1 * | 6/2011 | Paul | A61B 6/032 378/4 |
| 2011/0168878 A1 * | 7/2011 | Hoerndler | G06T 11/005 250/252.1 |
| 2012/0025826 A1 * | 2/2012 | Zhou | G01R 33/4833 324/309 |
| 2012/0093280 A1 * | 4/2012 | Konno | A61B 6/032 378/7 |
| 2012/0093282 A1 * | 4/2012 | Kappler | A61B 6/032 378/18 |
| 2012/0155617 A1 * | 6/2012 | Dutta | A61B 6/032 378/207 |
| 2012/0201438 A1 * | 8/2012 | Vermandel | G01N 29/0654 382/128 |
| 2013/0225958 A1 * | 8/2013 | Ichihara | A61B 6/481 600/363 |
| 2014/0079184 A1 * | 3/2014 | Das | A61B 6/484 378/62 |
| 2014/0266198 A1 * | 9/2014 | Tadic | G01R 33/387 324/309 |
| 2014/0321608 A1 * | 10/2014 | Ueki | A61B 6/032 378/18 |
| 2015/0212219 A1 * | 7/2015 | Cerello | A61B 6/583 702/104 |
| 2017/0296132 A1 * | 10/2017 | Manak | A61B 6/5282 |

FOREIGN PATENT DOCUMENTS

| | | |
|---|---|---|
| JP | 2005-058758 | 3/2005 |
| JP | 2008-136800 | 6/2008 |
| JP | 2008-161690 | 7/2008 |
| JP | 2011-239830 | 12/2011 |
| JP | 2012-125567 | 7/2012 |
| JP | 2013-017594 | 1/2013 |

OTHER PUBLICATIONS

Yuki Kanamori et al. "Calibration Phantom for Generation of the Quantitative Myocardial Perfusion Images Using Angiography in Coronary Angiography Laboratory", 70th Annual Scientific Congress of the Japanese Society of Radiological Technology, 2014, 3 pages.

Office Action dated Jul. 24, 2018, in Japanese Patent Application No. 2014-225100.

* cited by examiner (A)  (B)

X-RAY CONTRAST IMAGE

X-RAY CONTRAST IMAGE

X-RAY CONTRAST IMAGE

US 10,169,845 B2

MEDICAL IMAGE PROCESSING APPARATUS, X-RAY DIAGNOSTIC APPARATUS, PHANTOM, AND MEDICAL IMAGE PROCESSING METHOD

CROSS REFERENCES TO RELATED APPLICATIONS

This application is based upon and claims the benefit of priority from Japanese Patent Application No. 2013-268127, filed on Dec. 25, 2013; the entire contents of which are incorporated herein by reference.

Further, the entire contents of Japanese Patent Application No. 2014-225100, filed on Nov. 5, 2014 are incorporated herein by reference.

FIELD

Embodiments described herein relate generally to a medical image processing apparatus, an X-ray diagnostic apparatus, a phantom, and a medical image processing method.

BACKGROUND

In a perfusion examination of blood using an X-ray diagnostic apparatus, it is often important to quantitatively measure concentrations of a contrast agent injected into an object. Especially, in a perfusion examination of tissues, it is necessary to quantify concentrations of a contrast agent in each region.

Then, various corrections for suppressing influences by scattered X-rays, beam hardening, a respiratory motion, a fluctuation in a product (mAs) of a tube current supplied to an X-ray tube and an exposure time of an X-ray, and the like are performed in order to estimate concentrations of a contrast agent with a sufficient accuracy. In addition, calibrations are performed in advance in order to perform various corrections.

An object of the present invention is to quantitatively estimate concentrations of a contrast agent more simply with a higher accuracy.

DETAILED DESCRIPTION

In general, according to one embodiment, a medical image processing apparatus includes an image acquisition part and a data processing part. The image acquisition part is configured to obtain X-ray image data of an object including not less than three phantoms whose X-ray absorption factors are different from each other. The data processing part is configured to generate corrected X-ray image data of the object by correcting the obtained X-ray image data or other X-ray image data. The obtained X-ray image data or the other X-ray image data are corrected using a nonlinear function obtained based on pixel values of the obtained X-ray image data. The pixel values correspond to the phantoms.

Further, according to another embodiment, an X-ray diagnostic apparatus includes an imaging system and a data processing part. The imaging system is configured to acquire X-ray image data of an object including not less than three phantoms whose X-ray absorption factors are different from each other. The data processing part is configured to generate corrected X-ray image data of the object by correcting the acquired X-ray image data or other X-ray image data. The acquired X-ray image data or the other X-ray image data are corrected using a nonlinear function obtained based on pixel values of the acquired X-ray image data. The pixel values correspond to the phantoms.

Further, according to another embodiment, a phantom includes not less than three matters and an instrument. The three matters have X-ray absorption factors different from each other and equivalent to X-ray absorption factors corresponding to different concentrations of a contrast agent. The instrument is configured to set the matters in an imaging area of an X-ray image.

Further, according to another embodiment, a medical image processing method includes obtaining X-ray image data of an object including not less than three phantoms whose X-ray absorption factors are different from each other; and generating corrected X-ray image data of the object by correcting the obtained X-ray image data or other X-ray image data. The obtained X-ray image data or the other X-ray image data are corrected using a nonlinear function obtained based on pixel values of the obtained X-ray image data. The pixel values correspond to the phantoms.

A medical image processing apparatus, an X-ray diagnostic apparatus, a phantom, and a medical image processing method according to embodiments of the present invention will be described with reference to the accompanying drawings.

(First Embodiment)

Figure 1:
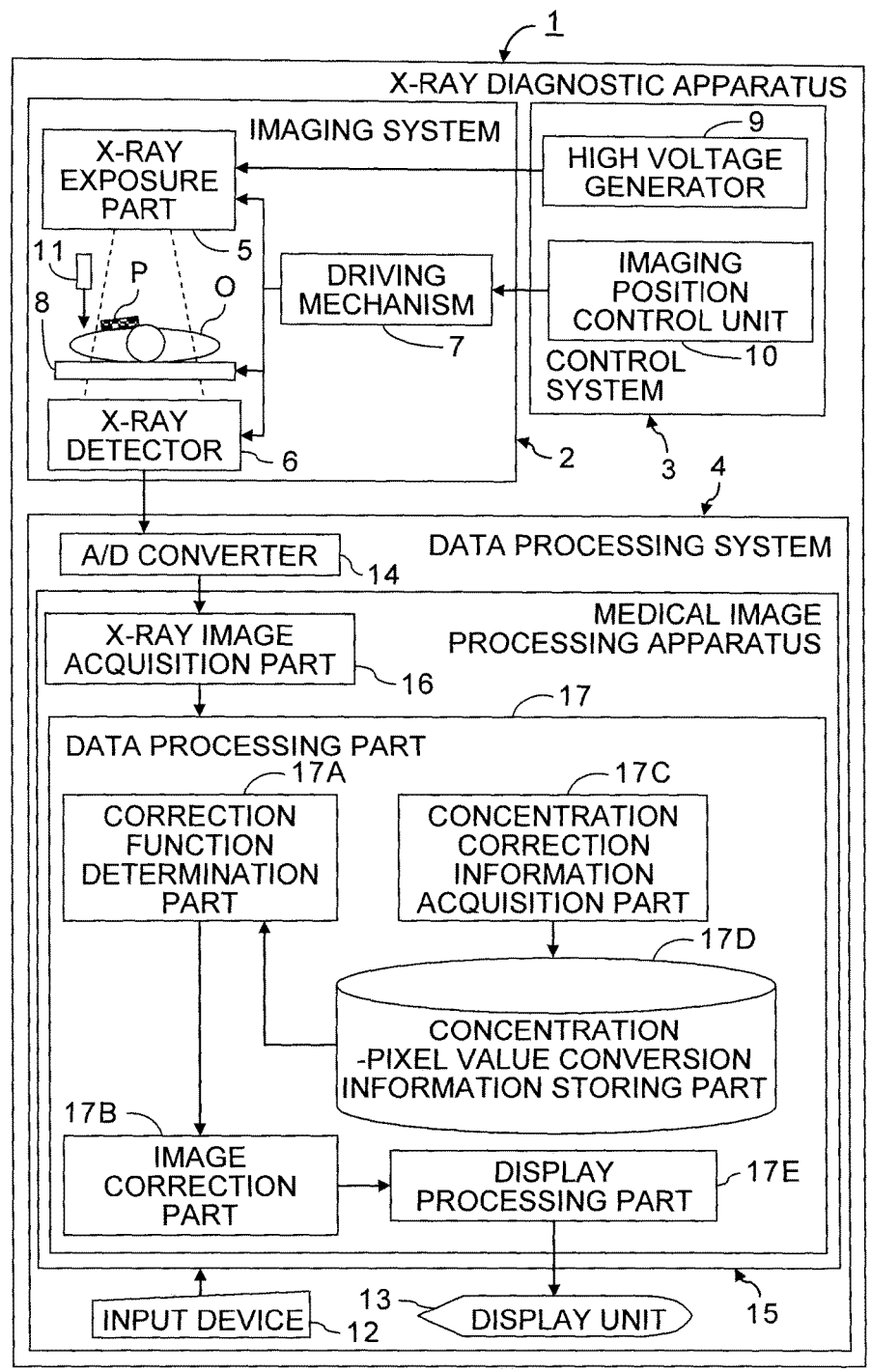
FIG. 1 is a configuration diagram of an X-ray diagnostic apparatus and a medical image processing apparatus according to the first embodiment of the present invention.

FIG. 1 is a configuration diagram of an X-ray diagnostic apparatus and a medical image processing apparatus according to the first embodiment of the present invention.

The X-ray diagnostic apparatus 1 includes an imaging system 2, a control system 3, and a data processing system 4. The imaging system 2 has an X-ray exposure part 5, an X-ray detector 6, a driving mechanism 7, and a bed 8. The control system 3 has a high voltage generator 9 and an imaging position control unit 10.

The X-ray exposure part 5 has an X-ray tube, and is placed opposite to the X-ray detector 6 so that an object O set on the bed 8 lies between the X-ray exposure part 5 and the X-ray detector 6. The X-ray exposure part 5 and the X-ray detector 6 can change the angle and relative position to the object O, with keeping their relative position, by the drive of the driving mechanism 7. Specifically, the X-ray exposure part 5 and the X-ray detector 6 are fixed to the both ends of a C-shaped arm having a rotation function. Then, the X-ray exposure part 5 is configured to expose an X-ray from a predetermined angle toward the object O with the X-ray tube while the X-ray detector 6 is configured to detect the X-ray transmitting the object O.

Moreover, the inclination and position of a top plate of the bed 8 can be adjusted with the driving mechanism 7. Therefore, the exposure direction of X-ray to the object O can be changed by adjusting the angle of the top plate as well as the angle of the X-ray exposure part 5 and the X-ray detector 6 to the object O.

Furthermore, near the object O set on the bed 8, a contrast agent injector 11 for injecting a contrast agent into the object O is placed. In addition, phantoms P simulating a contrast agent with predetermined concentrations are placed near the object O.

The high voltage generator 9 of the control system 3 is a unit which applies a high voltage to the X-ray tube of the X-ray exposure part 5 to expose an X-ray having a desired energy toward the object O. The imaging position control unit 10 is a unit which outputs a control signal to the driving mechanism 7 to control the driving mechanism 7. That is, the inclination and position of the top plate of the bed 8, and the rotation angle and position of the X-ray exposure part 5 and the X-ray detector 6 are controlled by the control signal output to the driving mechanism 7 from the imaging position control unit 10.

The data processing system 4 has an input device 12, a display unit 13, an A/D (analog to digital) converter 14, and a medical image processing apparatus 15. That is, the medical image processing apparatus 15 is built in the X-ray diagnostic apparatus 1. However, an independent medical image processing apparatus having similar functions may be connected to the X-ray imaging apparatus 1 through a network. The medical image processing apparatus 15 built in the X-ray diagnostic apparatus 1 or a medical image processing apparatus connected with the X-ray diagnostic apparatus 1 through a network can be configured by a computer reading a medical image processing program. However, circuits may be used for configuring the medical image processing apparatus 15 built in the X-ray diagnostic apparatus 1 or the medical image processing apparatus connected with the X-ray diagnostic apparatus 1 through a network.

A medical image processing program can be recorded on an information recording medium to be distributed as a program product so that a general purpose computer, such as a workstation, can be used as the medical image processing apparatus 15. As a matter of course, a medical image processing program may also be downloaded to a computer via a network, without an information recording medium.

The medical image processing apparatus 15 has an X-ray image acquisition part 16 and a data processing part 17. Moreover, the data processing part 17 has a correction function determination part 17A, an image correction part 17B, a concentration correction information acquisition part 17C, a concentration-pixel value conversion information storing part 17D, and a display processing part 17E. Therefore, the medical image processing program functions the computer as the X-ray image acquisition part 16 and the data processing part 17.

The X-ray image acquisition part 16 has a function to take in digitized X-ray detection data from the X-ray detector 6 through the A/D converter 14 and generate X-ray image data by necessary data processing. Therefore, when X-ray image data are generated based on X-ray detection data acquired in a state where a contrast agent has been injected into an object O, X-ray contrast image data can be obtained.

Especially, an object O can be imaged with not less than three phantoms P, whose X-ray absorption factors are different from each other, in a state where a contrast agent has been injected into the object O, by the imaging system 2. In this case, X-ray contrast image data of an object O including not less than three phantoms P, whose X-ray absorption factors are different from each other, are acquired by the imaging system 2. Therefore, X-ray contrast image data of an object O including not less than three phantoms P, whose X-ray absorption factors are different from each other, are also obtained at the X-ray image acquisition part 16.

The data processing part 17 has a function to perform necessary data processing of X-ray image data obtained in the X-ray image acquisition part 16, to generate X-ray image data for a display. Especially, the data processing part 17 has a function to generate corrected X-ray contrast image data of an object O, by correcting X-ray contrast image data using a nonlinear function obtained based on pixel values of X-ray contrast image data corresponding to phantoms P.

The correction function determination part 17A has a function to obtain a nonlinear function for correcting X-ray contrast image data, based on pixel values of X-ray contrast image data corresponding to phantoms P. Examples of a nonlinear function include a high order function, a logarithmic function or an exponential function. It is appropriate to use a cubic equation, a quartic equation or a quintic equation as a nonlinear function, from a viewpoint of correcting X-ray contrast image data with a practical and sufficient accuracy. Hereinafter, a case where a nonlinear function is a quartic equation will be described.

Here, features of phantoms P will be described. Phantoms P are objects, simulating a contrast agent with different concentrations which have at least three values, used for a calibration of pixel values.

Therefore, phantoms P can be composed with not less than three matters, whose X-ray absorption factors are different from each other and equivalent to X-ray absorption factors corresponding to different concentrations of a contrast agent, and an instrument for setting the matters in an imaging area of X-ray images, together with an object O. Note that, each of matters themselves which have X-ray absorption factors corresponding to different concentrations of a contrast agent may also be called a phantom P. Hereinafter, each of matters which have different X-ray absorption factors is called a phantom P while a structural body composed with the matters, having different X-ray absorption factors, and an instrument, for setting the matters in an imaging area, is called a phantom set, in order to distinguish each other.

Figure 2:
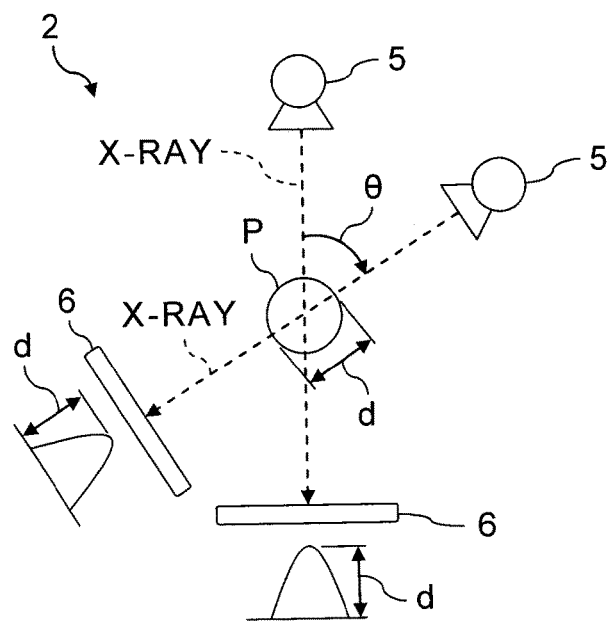
FIG. 2 shows transmission distances of X-rays in a case where a form of a phantom is a spherical configuration.

FIG. 2 shows transmission distances of X-rays in a case where a form of a phantom P is a spherical configuration.

Since the imaging system 2 rotates in the X-ray diagnostic apparatus 1, a phantom P is imaged in many directions from the X-ray exposure part 5. Therefore, when a phantom P is spherical, the distance d of an X-ray transmitting the center position of the phantom P is same as a diameter d of the phantom P, as shown in FIG. 2, regardless of X-ray exposure angles θ. That is, when a phantom P is spherical, the transmission distance d of an X-ray at the center position of the phantom P can be constant, whichever direction the X-ray is exposed from. Accordingly, a shape of phantom P is preferable to be spherical.

Hereinafter, description will be made for a case where a phantom P has a spherical shape. In this case, a nonlinear function for the correction of X-ray contrast image data can be obtained based on pixel values, of the X-ray contrast image data, at respective center positions of phantoms P each having a spherical shape.

When a phantom P is spherical, an appropriate diameter of the phantom P is approximately from 2 mm to 10 mm. This is because an excessively small sized phantom P causes influence of scattered rays to be too large while an excessively large sized phantom P causes influence of scattered rays to be too small. Furthermore, a desirable size of a phantom P is equivalent to that of an object which is an imaging target. For example, the diameter of a coronary artery of a heart is 2 mm to 4 mm, and the thickness of a myocardium is approximately 10 mm.

Therefore, although a same size of phantoms P leads to simplification of data processing, the phantoms P may have different diameters corresponding to sizes of imaging parts, as long as the sizes of the phantoms P are known.

Figure 3:
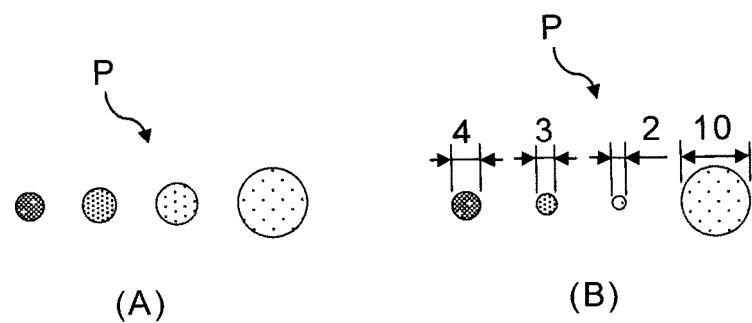
FIG. 3 shows an example case where sizes of phantoms are different from each other.

FIG. 3 shows an example case where sizes of phantoms P are different from each other.

For example, sizes of phantoms P may be changed according to simulated concentrations of a contrast agent as shown in FIG. 3 (A). Clinically, a contrast agent having a high concentration is injected into a blood vessel. The injected contrast agent diffuses in the process to reach tissues through thin blood vessels and capillaries. Thereby, the concentration of the contrast agent becomes low. Accordingly, a size of a phantom P which simulates a contrast agent with a high concentration can be small while a size of a phantom P which simulates a contrast agent with a low concentration can be large. Thus, a contrast agent, whose concentration becomes lower depending on an increase in a volume of the contrast agent by a diffusion, can be simulated by phantoms P whose X-ray absorption factors are different from each other.

As another example shown in FIG. 3 (B), sizes of phantoms P may be also determined according to sizes of imaging parts. When an imaging part is a heart, a contrast agent with the highest concentration of 300-370 [mgI/ml] is injected into a coronary artery whose diameter is approximately 2 mm to 4 mm. Then, the concentration of the contrast agent attenuates and becomes 100-300 [mgI/ml] in a thin blood vessel whose diameter is about 1 mm. Furthermore, when the contrast agent reaches a myocardium whose thickness is about 10 mm, the concentration of the contrast agent becomes not more than 100 [mgI/ml].

Accordingly, the higher the concentration is, the larger a diameter of a phantom P which simulates a concentration higher than 100 [mgI/ml] can be, in the range of approximately 2 mm to 4 mm. Meanwhile, a diameter of a phantom P which simulates a concentration not more than 100 [mgI/ml] can be about 10 mm. Thereby, a contrast agent, which is injected into a coronary artery and reaches a heart, can be simulated by phantoms P whose X-ray absorption factors are different from each other.

As described above, phantoms P being elements of a phantom set can consist of specimens which have sizes according to at least one of different X-ray absorption factors corresponding to concentrations of a contrast agent and sizes of imaging parts into which a contrast agent flows.

Next, structural examples of phantom sets, each consisting of phantoms P and an instrument for setting the phantoms P, will be described.

Figure 4:
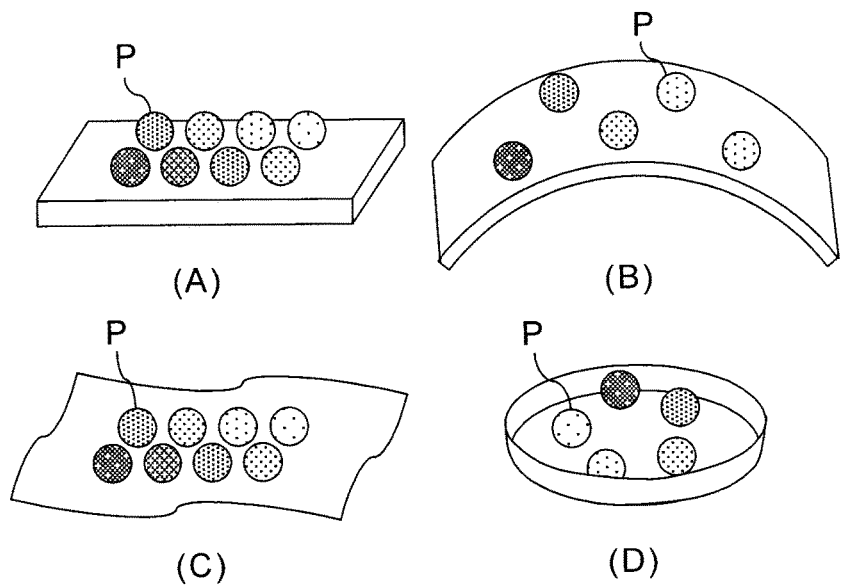
FIG. 4 shows structural examples of phantom sets each classified into a type which supports phantoms.

FIG. 4 shows structural examples of phantom sets each classified into a type which supports phantoms P.

A phantom set can be composed by attaching phantoms P on a flat plate support as shown in FIG. 4 (A), a plate support curved to fit a human body surface as shown in FIG. 4 (B), a flexible sheet support as shown in FIG. 4 (C), or an edged plate support as shown in FIG. 4 (D). That is, an instrument for setting phantoms P can be made as a support of the phantoms P. As a matter of course, the instrument may have a function as a support having concaves or partitions to prevent phantoms P from moving. Note that, an instrument for setting phantoms P consists of materials which can be considered as X-ray non-absorbable materials.

Figure 5:
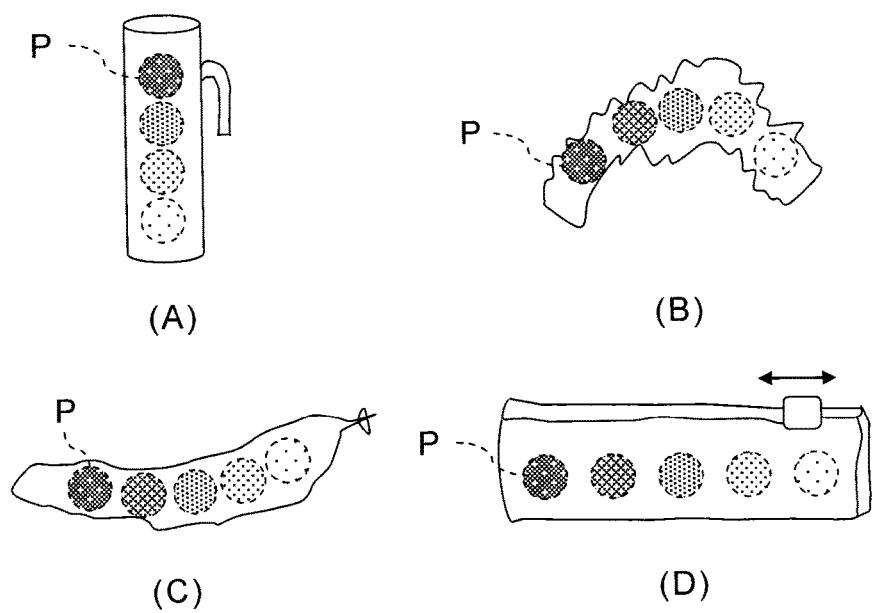
FIG. 5 shows structural examples of phantom sets each classified into a type which houses phantoms.

FIG. 5 shows structural examples of phantom sets each classified into a type which houses phantoms P.

An instrument for setting phantoms P may be a housing body having various structures, such as a bottomed tubular housing body as shown in FIG. 5 (A), a tubular housing body having flexibility with closed ends as shown in FIG. 5 (B), a long bag-like housing body as shown in FIG. 5 (C), or a housing body having an opening and closing function as shown in FIG. 5 (D).

Figure 6:
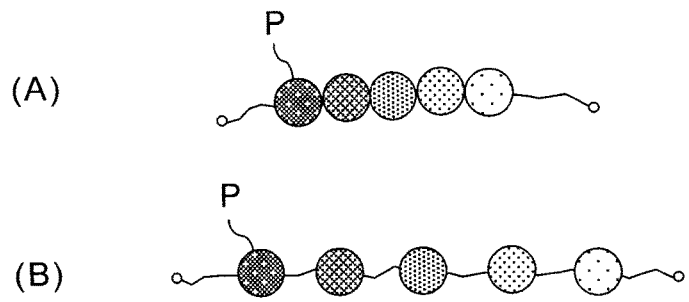
FIG. 6 shows structural examples of phantom sets each classified into a type which connects phantoms with each other.

FIG. 6 shows structural examples of phantom sets each classified into a type which connects phantoms P with each other.

An instrument for setting phantoms P may also be a stringlike member for setting connected phantoms P as shown in FIG. 6 (A) or a stringlike member for connecting phantoms P at intervals as shown in FIG. 6 (B).

As exemplified in FIG. 4, FIG. 5 and FIG. 6, the instrument for setting phantoms P can have a structure for putting on the phantoms P, a structure for housing the phantoms P, or a structure for connecting the phantoms P. Furthermore, the instrument for setting phantoms P may also have a structure for setting phantoms P with mobility. Movable phantoms P allow imaging of the phantoms P at different positions.

Figure 7:
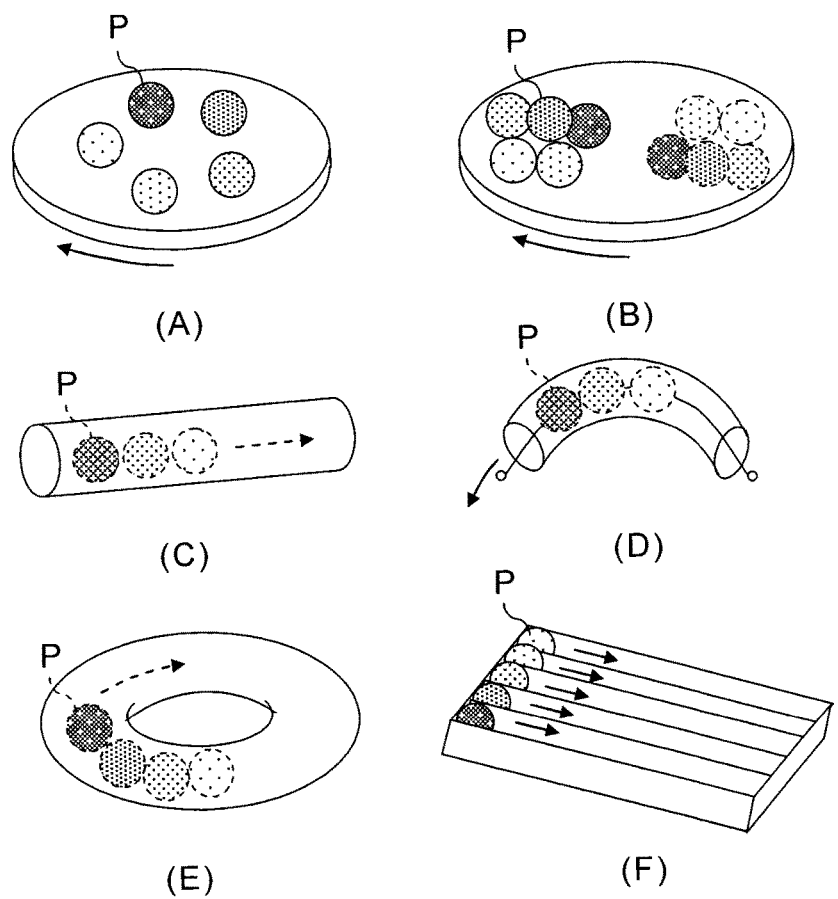
FIG. 7 shows structural examples of phantom sets each classified into a type which allows translations of phantoms.

FIG. 7 shows structural examples of phantom sets each classified into a type which allows translations of phantoms P.

As shown in FIG. 7 (A), phantoms P can be fixed to a rotatable platy instrument. In this case, when phantoms P are fixed to positions away from the rotation center as shown in FIG. 7 (B), movement distances of the phantoms P can be lengthened.

As other examples, phantoms P may move inside a cylindrical instrument as shown in FIG. 7 (C), a curved cylindrical instrument as shown in FIG. 7 (D), or a doughnut-shaped cylindrical instrument as shown in FIG. 7 (E). Furthermore, as another example shown in FIG. 7 (F), spherical phantoms P set on an instrument with many grooves can roll and move by inclination of the instrument.

A tabular instrument on which phantoms P are fixed as shown in FIG. 7 (A) or (B) can be rotated to a predetermined position manually using a bearing as an element. Alternatively, a power source, such as a motor, may be connected to a bearing so that a tabular instrument can rotate automatically.

On the other hand, in case of moving phantoms P inside a tubular instrument as shown in FIG. 7 (C), (D), or (E), it is possible to change positions of the respective phantoms P in a similar manner to an operation of a catheter, by connecting the phantoms P with each other using a stringlike member as shown in FIG. 6. Alternatively, it is also possible to move each phantom P by inserting unconnected phantoms P inside a tubular instrument, and pouring a fluid with a syringe or the like. As a matter of course, phantoms P may be rolled and moved by the inertia force due to inclination of a tubular instrument.

The preferable conditions required for phantoms P include that at least the center positions of the phantoms P do not overlap in an X-ray exposure direction.

Figure 8:
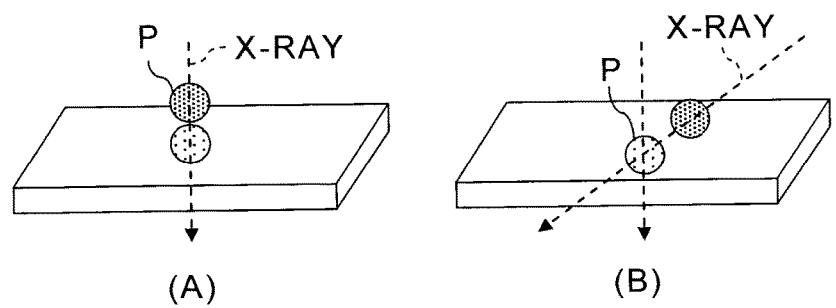
FIG. 8 shows examples of inappropriate arrangement of phantoms.

FIG. 8 shows examples of inappropriate arrangement of phantoms P.

As shown in FIG. 8 (A), it is inappropriate to arrange plural phantoms P on a tabular instrument in a direction perpendicular to an mounting plane since an X-ray transmits the plural phantoms P. Alternatively, as exemplified in FIG. 8 (B), it may be inappropriate to arrange phantoms P on a tabular instrument in a direction which is not perpendicular to an mounting plane since an X-ray exposure direction may change by driving of the driving mechanism 7, such as a C-shaped arm.

Accordingly, it is important to configure an instrument for setting phantoms P so as to hold the phantoms P at spatial positions calculated so that at least respective center positions of the phantoms P are not on a same straight line in possible X-ray transmission directions.

Figure 9:
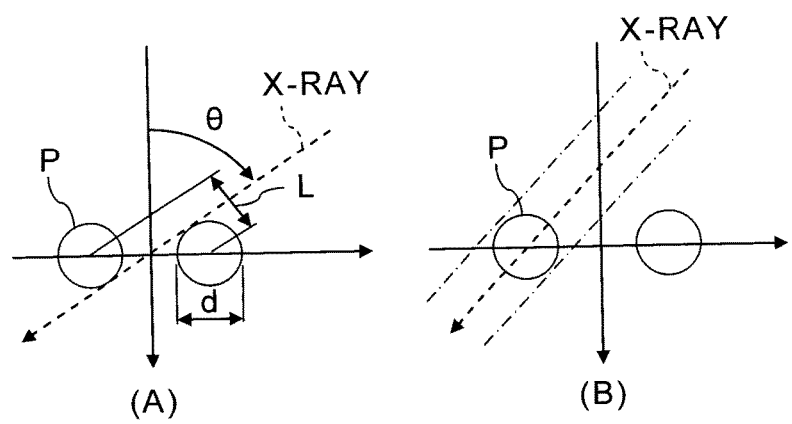
FIG. 9 shows examples of arrangement of phantoms for avoiding an inappropriate overlap thereof.

FIG. 9 shows examples of arrangement of phantoms P for avoiding an inappropriate overlap thereof.

As shown in FIG. 9 (A), the distance L between phantoms P can be geometrically calculated based on a practical inclined angle θ of C-shaped arm and a diameter d of phantom P so that the phantoms P do not overlap with each other in a projection direction of the phantoms P. When another phantom P is arranged outside the range shown with the dashed-dotted lines in FIG. 9 (B), plural phantoms P can be set at an appropriate interval. That is, even when a C-shaped arm is rotated, phantoms P can be arranged so as to avoid overlapping with each other in X-ray exposure directions.

It is appropriate to attach the above described instrument holding phantoms P as close to a human body surface as possible from a viewpoint of improving a correction accuracy. Therefore, a structure of an instrument for setting phantoms P is desirable to be one for setting phantoms P on a human body as an object O.

Figure 10:
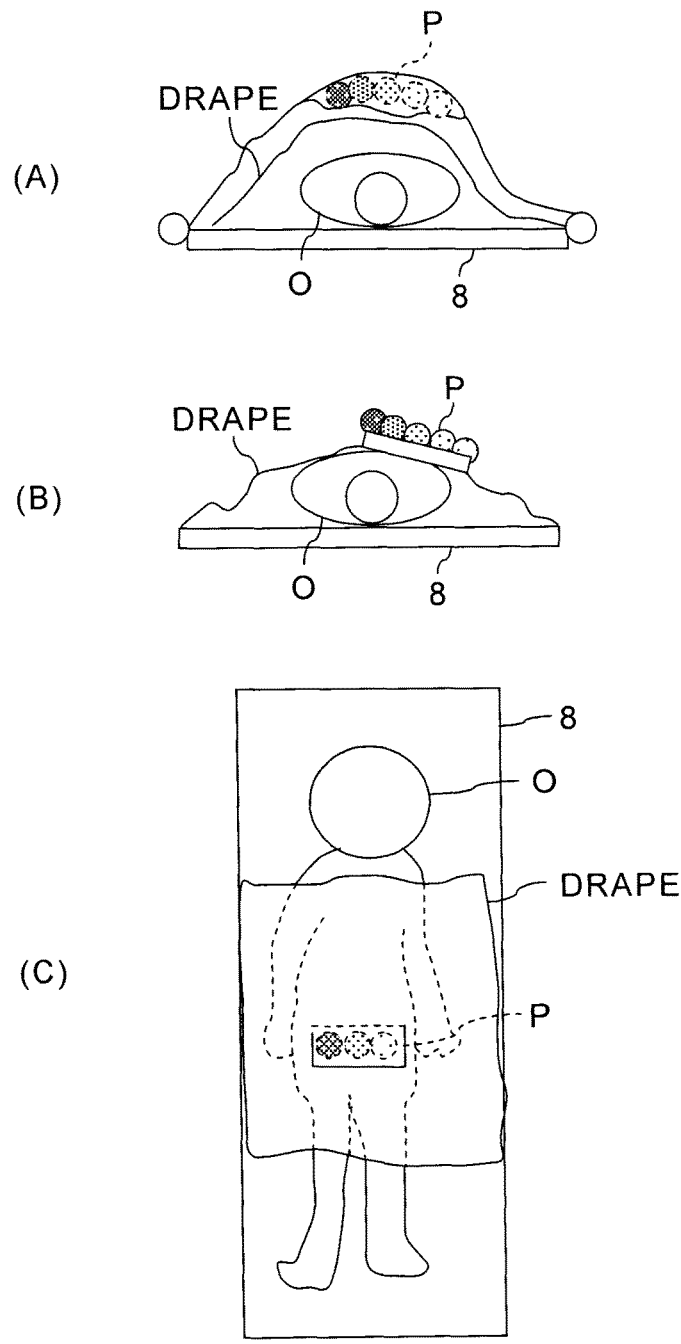
FIG. 10 is a view for explaining examples of method for attaching phantoms on a body surface of a human body.

FIG. 10 is a view for explaining examples of method for attaching phantoms P on a body surface of a human body.

A human body as an object O set on the top plate of the bed 8 is covered with a drape. Thus, an instrument holding phantoms P can be placed outside a drape and fixed to rails of the bed 8 with rubber or the like, as shown in FIG. 10 (A). Alternatively, as shown in FIG. 10 (B), an instrument holding phantoms P can also be attached on a drape with adhesive tape or the like. Furthermore, as another example shown in FIG. 10 (C), an instrument holding phantoms P can also be housed in an openable pocket provided on the drape. The pocket can be opened and closed with a hook and loop fastener or the like, for example.

According to the above-mentioned attachment methods of phantoms P, the phantoms P can be fixed without slipping, in a state close to a human body surface. When phantoms P attached on a human body which is an object O are imaged, the correction function determination part 17A can obtain a correction function of X-ray contrast image data based on pixel values, corresponding to the phantoms P, of the X-ray contrast image data.

Figure 11:
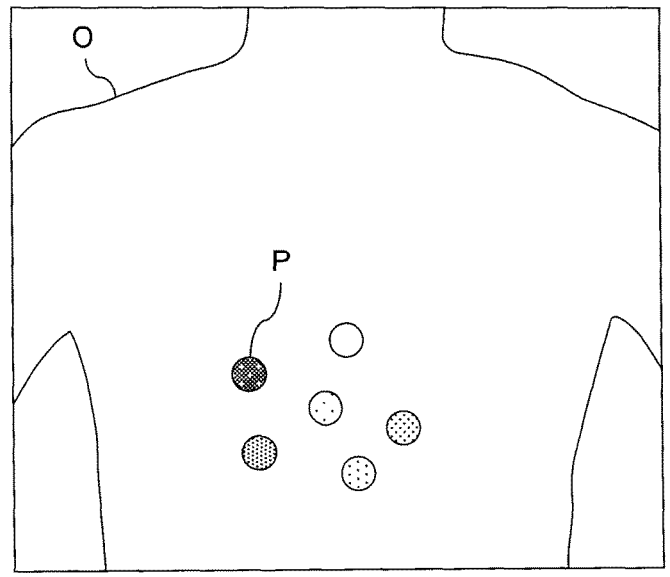
FIG. 11 shows an example of X-ray contrast image acquired by attaching six spherical phantoms, whose X-ray absorption factors are different from each other, to an object.

FIG. 11 shows an example of X-ray contrast image acquired by attaching six spherical phantoms P, whose X-ray absorption factors are different from each other, to an object O.

When plural phantoms P, whose X-ray absorption factors are different from each other, are imaged together with an object O with a contrast agent, the respective phantoms P are depicted with different pixel values corresponding to the X-ray absorption factors, as shown in FIG. 11. Then, it becomes possible to obtain a correction function of X-ray contrast image data based on the pixel values corresponding to the respective phantoms P.

When the correction function is a quartic equation, the correction function can be expressed by expression (1).

$$\tau\rho d = a_0 + a_1\{ln(I)\} + a_2\{ln(I)\}^2 + a_3\{ln(I)\}^3 + a_4\{ln(I)\}^4 \quad (1)$$

wherein τ represents a mass attenuation coefficient [cm²/g] of the contrast agent, ρ represents a concentration [g/cm³] of the contrast agent, d represents a diameter [cm] of a spherical region corresponding to corrected pixels, I represents each pixel value of the X-ray contrast image data before the correction, and $a_0$, $a_1$, $a_2$, $a_3$, $a_4$ represent coefficients.

Each coefficient $a_0$, $a_1$, $a_2$, $a_3$, $a_4$ shown in expression (1) can be calculated based on pixel values of phantoms P, whose mass attenuation coefficients τ are known, and X-ray absorption coefficients corresponding to concentrations ρ of the contrast agent. In case that the correction function is a quartic equation, the number of the coefficients $a_0$, $a_1$, $a_2$, $a_3$, $a_4$ to be calculated is five. Therefore, as long as pixel values I1, I2, I3, I4, I5 of at least five phantoms P, whose X-ray absorption coefficients are different from each other, can be measured, the coefficients $a_0$, $a_1$, $a_2$, $a_3$, $a_4$ of the correction function can be calculated by solving the simultaneous equations shown by expression (2-1), expression (2-2), expression (2-3), expression (2-4), and expression (2-5).

$$\tau\rho_1 d = a_0 + a_1\{ln(I1)\} + a_2\{ln(I1)\}^2 + a_3\{ln(I1)\}^3 + a_4\{ln(I1)\}^4 \quad (2\text{-}1)$$

$$\tau\rho_2 d = a_0 + a_1\{ln(I2)\} + a_2\{ln(I2)\}^2 + a_3\{ln(I2)\}^3 + a_4\{ln(I2)\}^4 \quad (2\text{-}2)$$

$$\tau\rho_3 d = a_0 + a_1\{ln(I3)\} + a_2\{ln(I3)\}^2 + a_3\{ln(I3)\}^3 + a_4\{ln(I3)\}^4 \quad (2\text{-}3)$$

$$\tau\rho_4 d = a_0 + a_1\{ln(I4)\} + a_2\{ln(I4)\}^2 + a_3\{ln(I4)\}^3 + a_4\{ln(I4)\}^4 \quad (2\text{-}4)$$

$$\tau\rho_5 d = a_0 + a_1\{ln(I5)\} + a_2\{ln(I5)\}^2 + a_3\{ln(I5)\}^3 + a_4\{ln(I5)\}^4 \quad (2\text{-}5)$$

Figure 12:
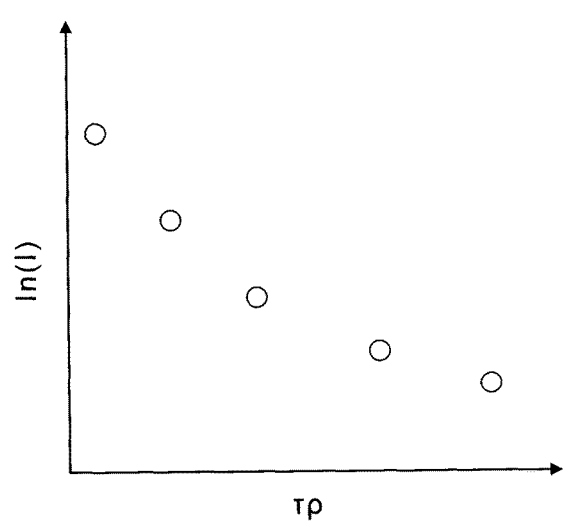
FIG. 12 is a graph which shows a relation between pixel values of a phantom P and a correction function.

FIG. 12 is a graph which shows a relation between pixel values of a phantom P and a correction function.

In FIG. 12, the horizontal axis represents the values τρ after the correction by the correction function, and the vertical axis represents the natural logarithmic values ln(I)

of the pixel values before the correction by the correction function. When the respective natural logarithmic values of the pixel values I1 I2, I3, I4, and I5 of the five phantoms P and the corrected values $\tau\rho_1$, $\tau\rho_2$, $\tau\rho_3$, $\tau\rho_4$, and $\tau\rho_5$, which are the products of the mass attenuation coefficient $\tau$ with the concentrations $\rho_1$, $\rho_2$, $\rho_3$, $\rho_4$, and $\rho_5$ of contrast agent simulated by the respective phantoms P, are plotted on their corresponding positions, a result is obtained as shown in FIG. 12. Then, the quartic function that passes through the respective plotted points is the correction function.

Figure 13:
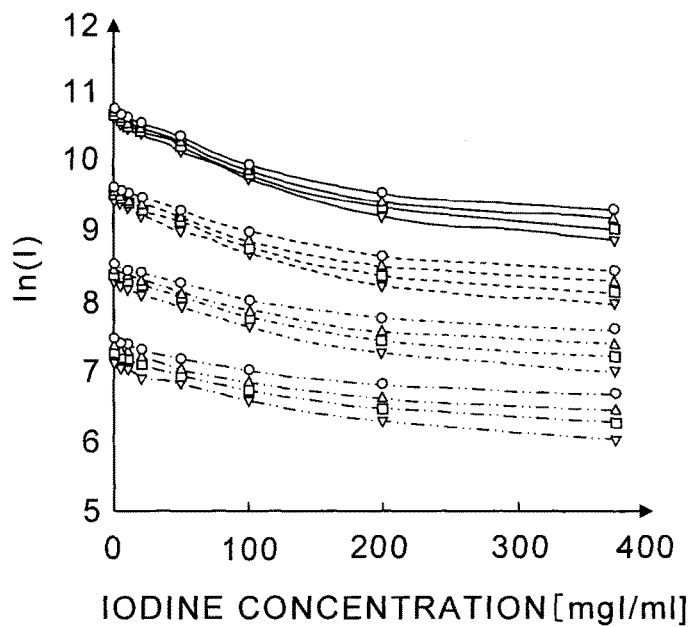
FIG. 13 is a graph which shows relations between true values of concentrations of a contrast agent and measured values thereof as pixel values.

FIG. 13 is a graph which shows relations between true values of concentrations of a contrast agent and measured values thereof as pixel values.

In FIG. 13, the horizontal axis represents the concentrations [mgI/ml] of Iodine used as the contrast agent, and the vertical axis represents natural logarithmic values of relative pixel values of X-ray contrast image data acquired by setting a constant tube voltage of the X-ray tube.

The difference in the line types used for the curves in FIG. 13 indicates the difference in SIDs (source image distances), and the difference in the plotted shapes in FIG. 13 indicates the difference in the body thicknesses of the object O. Note that, the SID is defined as a distance between the focal point of the X-ray tube included in the X-ray exposure part 5 and a detector plane of the X-ray detector 6.

As shown in FIG. 13, even when the concentrations of the contrast agent are the same, the image signal values of the X-ray image data change depending on the body thicknesses of the object O and the SIDs. Therefore, in order to obtain concentrations of a contrast agent correctly, a correction to remove factors, such as body thicknesses of an object O and SIDs, influencing image signal values of X-ray contrast image data, from the image signal values, is necessary. As factors influencing image signal values, scattered rays, beam hardening, variations in mAs, and respiratory motions can be mentioned in addition to body thicknesses of an object O and SIDs.

Accordingly, when image signal values and concentration values of a contrast agent, corresponding to multiple phantoms P, are plotted as shown in FIG. 12, a relational expression between the concentrations of the contrast agent and the image signal values, reflecting respective factors, such as body thicknesses of an object O, SIDs, scattered rays, beam hardening, variations in mAs, and respiratory motions, can be obtained. Consequently, the obtained relational expression can be used as a correction function for calculating quantitative concentration values of a contrast agent based on image signal values.

That is, a not less than third order inverse function for calculating true values of concentrations of a contrast agent based on image signal values observed as measured values of concentrations of the contrast agent can be obtained as the correction function based on a relation between image signal values and concentration values of a contrast agent, corresponding to multiple phantoms P. Note that, in a case that a temporal variation or temporal variations, such as variations in mAs and respiratory motions, are also corrected, each coefficient of the correction function also changes temporally.

As shown in FIG. 12 and FIG. 13, the curvature of the correction function is not constant. Moreover, a concentration range, in which obtaining concentrations of a contrast agent with a high accuracy is required, is occasionally local. Accordingly, the plotted points may also be arranged at unequal intervals in order to obtain the correction function with a sufficient accuracy. That is, a nonlinear function can be obtained based on pixel values of phantoms P corresponding to multiple X-ray absorption factors distributed at unequal intervals.

X-ray absorption factors of phantoms P corresponding to practical concentrations of a contrast agent are about 0-370 [mgI/ml]. Moreover, when a contrast agent is administered to a heart, a high accuracy is required in the concentration range of 0-100 [mgI/ml]. Accordingly, concentration intervals of phantoms P may be narrowed in the concentration range of 0-100 [mgI/ml] while the concentration intervals of the phantoms P may be widened in the concentration range of more than 100 [mgI/ml], for example.

Especially, when the correction function is estimated as a fifth order expression like the above-mentioned example, making multiple concentration values of a contrast agent for calculating the coefficients have unequal intervals occasionally improves the accuracy. Moreover, it is convenient to set an X-ray absorption factor of one phantom P, among multiple phantoms P, to 0 [mgI/ml], from a viewpoint of maintaining the accuracy.

Moreover, it is appropriate to set the number of phantoms P, determined according to the degree of the correction function and the number of the coefficients to be obtained, to about 3-8 pieces. This is because a small number of phantoms P lead to reduction in the correction accuracy since the degree of the correction function becomes small, while an excessive number of phantoms P lead to reduction in the visibility of an imaging part since an area occupied by the phantoms P in an imaging region becomes large. As mentioned above, it is appropriate for the correction function to be a third degree expression, a fourth degree expression, or a fifth degree expression, from a viewpoint of the accuracy. Therefore, it is appropriate that the number of phantoms P should be about five practically.

Accordingly, an example case where the number of phantoms P is five will be described henceforth.

As mentioned above, even when a concentration of contrast agent is constant, image signal values change depending on body thicknesses of an object O. Especially, the influence of beam hardening changes also depending on body thicknesses. Therefore, when an abdomen or the like whose body thicknesses can be considered to be constant is imaged, errors in concentrations of a contrast agent due to differences in the body thicknesses are negligible. However, when an imaging part whose body thicknesses are not considered to be constant is imaged, a correction of image signal values according to the body thicknesses is desired.

For example, difference in body thicknesses is remarkable in some imaging parts, such as a head, a lung, and a lower limb. Moreover, even in a case of an abdomen, transmission distances of X-rays in an object O become non-uniform when the exposure direction of the X-rays changes.

Accordingly, an imaging region may be divided into multiple regions so that a different correction function can be obtained for each divided region. For that purpose, what is necessary is to acquire multiple frames of X-ray contrast image data with moving a phantom set composed of multiple phantoms P or acquire at least one frame of X-ray image data with arranging phantom sets, each composed of multiple phantoms P, at multiple positions.

Figure 14:
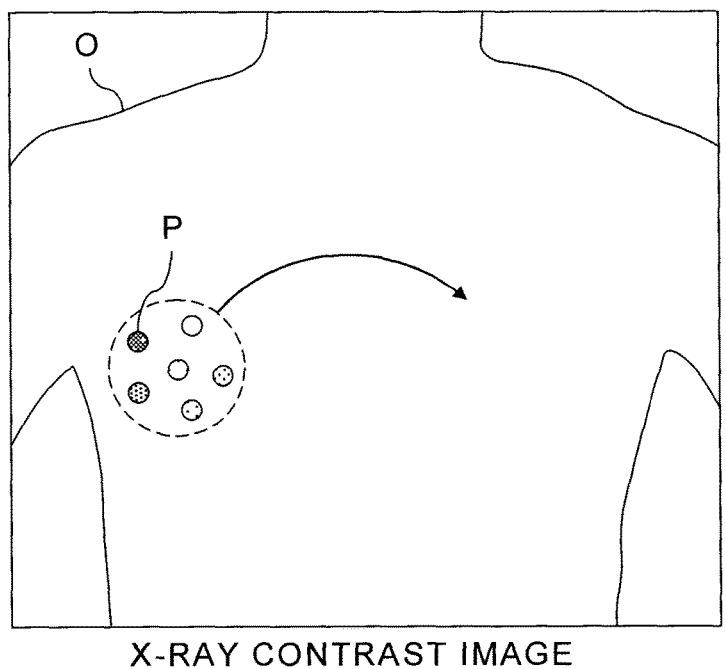
FIG. 14 shows an example of moving a phantom set having phantoms.

FIG. 14 shows an example of moving a phantom set having phantoms P.

As shown in FIG. 14, a position of a phantom set composed of multiple phantoms P can be changed for each frame of X-ray image data. Consequently, multiple frames of X-ray image data can be acquired in the condition that the phantom set composed of the multiple phantoms P has been arranged in different regions. Then, multiple nonlinear functions corresponding to the different regions can be acquired, as the correction functions, based on the acquired multiple frames of the X-ray image data, and the respective corrections for the different regions can be performed using the multiple nonlinear functions.

In this case, the phantom set has a structure that can move the multiple phantoms P as illustrated in FIG. 7. Then, the multiple phantoms P are sequentially moved in multiple regions in which body thicknesses of an object O in an exposure direction of X-rays can be considered to be different, and X-ray imaging is repeatedly performed. The movements of the phantoms P can be performed by an arbitrary way, such as rotation movements, translation movements, and/or random movements.

Note that, the phantom set may not be moved in all the regions, where the body thicknesses of the object O in the exposure direction of X-rays can be considered to be different, but be moved only in a part of the regions, in order to acquire the frames of the X-ray image data. In that case, the correction functions can be obtained, only for the regions where the phantom set has been moved, based on the pixel values of the phantoms P. Then, the correction functions corresponding to the regions where the phantom set has not been moved can be obtained by interpolation based on the multiple correction functions corresponding to the regions where the phantom set has been moved.

That is, so long as the phantom set is moved to necessary regions and X-ray imaging of the necessary regions is performed, the correction functions corresponding to all the regions can be obtained by calculation without moving the phantom set to all the regions to perform X-ray imaging. In this case, the correction functions corresponding to all the regions are obtained based on pixel values of X-ray image data whose number of frames are smaller than the number of the regions.

Figure 15:
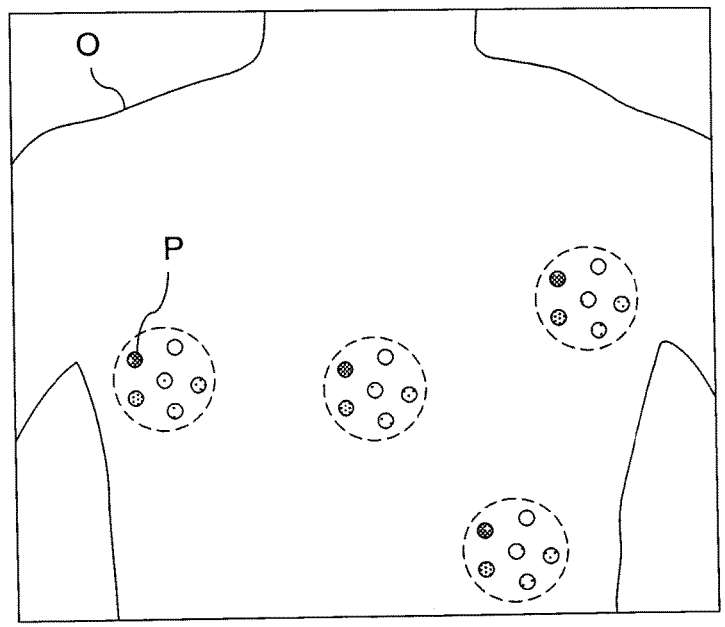
FIG. 15 shows an example of arranging plural phantom sets, each having phantoms, at plural positions.

FIG. 15 shows an example of arranging plural phantom sets, each having phantoms P, at plural positions.

As shown in FIG. 15, one frame of X-ray image data can be acquired in a condition that phantom sets, each composed of multiple phantoms P, have been arranged in different regions respectively. Consequently, multiple nonlinear functions corresponding to the different regions can be obtained, as the correction functions, based on the acquired one frame of the X-ray image data so that the respective corrections for the different regions can be performed using the multiple nonlinear functions.

It is appropriate for the arrangement positions of the phantom groups to be inside multiple regions in which body thicknesses of an object O in an exposure direction of X-rays can be considered to be different, as mentioned above. Accordingly, multiple phantoms P can be arranged at a position on an internal organ that a doctor is interested in so that the visibility of a part of interest should not be spoiled, for example. Moreover, in order to secure the visibility of a part of interest, it is desired that phantoms P having small sizes are arranged.

In a case of a routine study, positions that are not focused regions are roughly determined on an X-ray image. Accordingly, it is preferred for the instrument for arranging multiple phantoms P to have a structure allowing an arrangement of the multiple phantoms P in regions other than focused regions of an object O.

When the single or multiple correction functions have been obtained as mentioned above, X-ray contrast image data can be corrected. Note that, when influences by temporal changes in imaging conditions are corrected, multiple time series correction functions are obtained, for a common region, based on multiple time series frames of X-ray image data.

The image correction part 17B has a function to correct each frame of X-ray contrast image data using a correction function or correction functions obtained as a nonlinear function or nonlinear functions, such as a fourth order expression, in the correction function determination part 17A. Specifically, when a phantom set has been arranged at one position and a correction function has been obtained without dividing an imaging region, all the pixel values in the imaging region are corrected by the correction function. Meanwhile, when multiple correction functions corresponding to multiple regions have been obtained from a single frame or multiple frames of X-ray image data in which a phantom set or phantom sets have been arranged at different positions, all the pixel values in each region are corrected by the correction function corresponding to the region.

Moreover, in a case that time series correction functions common to an imaging region have been obtained, and alternatively, in a case that multiple correction functions corresponding to multiple regions have been obtained dynamically and repeatedly, pixel values are also corrected in the time direction by the correction functions.

Thereby, signal values from which influences by factors, such as body thicknesses of an object O, SIDs, scattered rays, beam hardening, variations in mAs, and respiratory motions, influencing image signal values have been removed can be calculated for all pixel positions. Therefore, X-ray contrast image data whose pixel values are correction function values $\tau \rho$ or concentrations $\rho$ of a contrast agent can be provided for a diagnosis, as corrected X-ray contrast image data.

By the way, errors actually exist in X-ray absorption factors, corresponding to concentrations of a contrast agent, of phantoms P. Moreover, when the errors in X-ray absorption factors are reduced as much as possible, manufacturing costs of phantoms P increase. In addition, X-ray absorption factors possibly change over time depending on materials of phantoms P. Therefore, it is desired to obtain correction functions on the assumption that errors exist in X-ray absorption factors of phantoms P.

Accordingly, the concentration correction information acquisition part 17C has a function to acquire information for correcting errors included in concentrations of a contrast agent simulated by phantoms P. The information for calibrating errors in X-ray absorption factors of phantoms P can be information, such as a function or a table, indicating a previously obtained relation between concentrations of a contrast agent and pixel values of X-ray image data.

Figure 16:
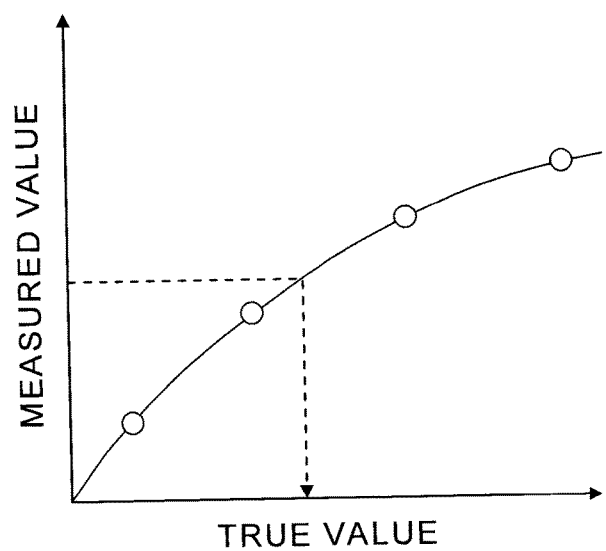
FIG. 16 is an example of graph which shows a relation between true values of concentrations of a contrast agent and image signal values of X-ray image data.

FIG. 16 is an example of graph which shows a relation between true values of concentrations of a contrast agent and image signal values of X-ray image data.

In FIG. 16, the horizontal axis represents true values of concentrations of a contrast agent, and the vertical axis represents measured values of the concentrations of the contrast agent, measured as image signal values by X-ray imaging. When X-ray imaging of a contrast agent having different concentrations is actually performed, plot data which indicate a relation between true values of the concentrations of the contrast agent and image signal values can be obtained as shown in FIG. 16. Therefore, a table or a function for obtaining a true value of a concentration of a contrast agent from an image signal value can be obtained using an approximating method, such as fitting.

As a specific example, plot data as shown in FIG. 16 can be obtained by X-ray imaging of syringes, whose respective diameters are about 10 mm, by which contrast agents having different concentrations have been suctioned.

The information, which indicates a relation between true values of concentrations of a contrast agent and image signal values, obtained by the concentration correction information acquisition part 17C can be stored in the concentration-pixel value conversion information storing part 17D. Then, The correction function determination part 17A is configured to calibrate an X-ray absorption factor of each phantom P by referring to the information stored in the concentration-pixel value conversion information storing part 17D, in prior to a determination of a correction function or correction functions. That is, in the correction function determination part 17A, a nonlinear function or nonlinear functions, in which influences by errors in X-ray absorption factors of multiple phantoms P have been corrected, can be obtained as a correction function or correction functions based on information which indicates a previously acquired relation between concentrations of a contrast agent and pixel values of X-ray image data.

When errors in X-ray absorption factors of phantoms P are corrected, X-ray imaging of the phantoms P to be calibrated is performed under same imaging conditions as imaging conditions, such as tube voltage, for previous X-ray imaging of a contrast agent. Consequently, true values of X-ray absorption factors of the phantoms P can be obtained based on image signal values of X-ray image data in which the phantoms P have been depicted. Specifically, the image signal values of the phantoms P can be converted into the X-ray absorption factors based on conversion information, between image signal values and X-ray absorption factors, stored in the concentration-pixel value conversion information storing part 17D.

By such a calibration of phantoms P themselves for calibrating X-ray contrast image data, a correction function or correction functions for the X-ray contrast image data can be obtained with high accuracy even in a case that the X-ray absorption factors of the phantoms P are not strictly accurate. For example, even in a case that a distributed phantom P whose X-ray absorption factor is indicated as 100 [mgI/ml] actually has 105 [mgI/ml] of X-ray absorption factor, a correction function or correction functions for X-ray contrast image data can be obtained correctly. That is, it is possible to obtain a correction function or correction functions using cheap phantoms P whose accuracies are rough.

Note that, a calibration of X-ray absorption factors of phantoms P can be performed before a contrast study or at periodical timings.

The display processing part 17E has functions to perform necessary display processing of X-ray image data acquired in the medical image processing apparatus 15, such as X-ray image data acquired by the X-ray image acquisition part 16, X-ray contrast image data corrected in the image correction part 17B, and the like, in order to generate two dimensional (2D) X-ray image data for display. The display processing part 17E also has a function to output the generated 2D X-ray image data for display to the display unit 13.

Next, an operation and action of the X-ray diagnostic apparatus 1 and the medical image processing apparatus 15 will be described.

Figure 17:
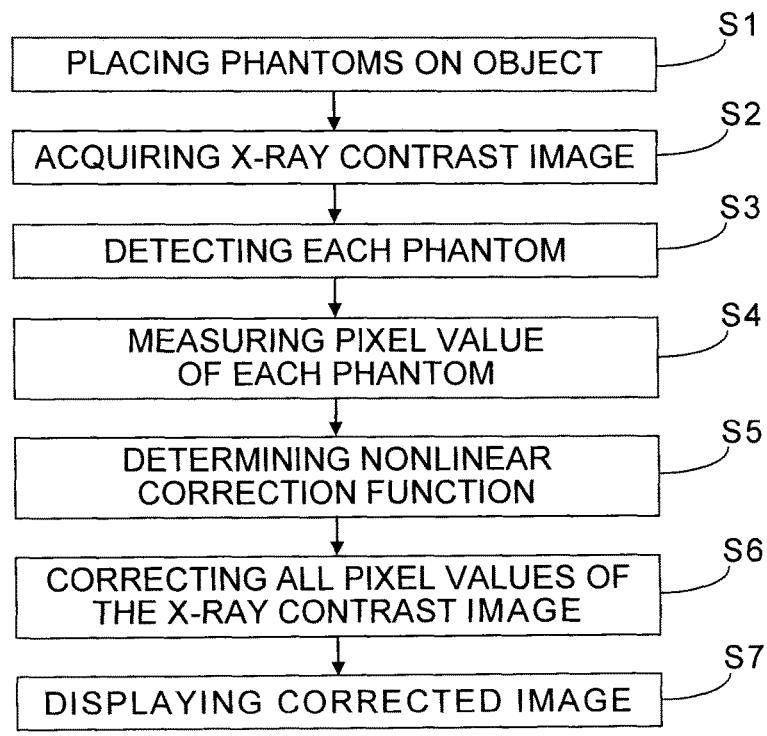
FIG. 17 is a flow chart which shows a flow of an operation and processing of the X-ray diagnostic apparatus and the medical image processing apparatus shown in FIG. 1.

FIG. 17 is a flow chart which shows a flow of an operation and processing of the X-ray diagnostic apparatus 1 and the medical image processing apparatus 15 shown in FIG. 1.

Firstly, in Step S1, multiple phantoms P whose X-ray absorption factors are different from each other are set on an object O. For a specific example, an instrument, which holds five spherical phantoms P, is set on the object O so as to be in a field of view for X-ray imaging. Preferably, at least one phantom set including the multiple phantoms P is arranged at a position where the phantom set lies inside the field of view during exposures of X-rays from possible X-ray exposure directions, at a time of a diagnosis or a treatment of the object O.

Next, in Step S2, imaging of X-ray contrast images is performed. For that purpose, the object O is set on the top plate of the bed 8. Then, the driving mechanism 7 is driven by control signals from the imaging position control unit 10. Thereby, the rotation angles and the positions of the X-ray exposure part 5 and the X-ray detector 6 in addition to the inclination and the position of the top plate of the bed 8 are adjusted according to an imaging part. At this time, the rotation angles and the positions of the X-ray exposure part 5 and the X-ray detector 6, and the inclination and the position of the top plate of the bed 8 are controlled so that the multiple phantoms P are also inside the field of view together with the part, such as an internal organ, as an examination target.

Meanwhile, a contrast agent is injected from the contrast agent injector 11 into the object O. Then, X-ray image data of the object O including the multiple phantoms P are acquired. The acquisition of the X-ray image data is performed by operations of the imaging system 2 under the control by the control system 3 and data processing in the data processing system 4. Specifically, a high voltage is applied to the X-ray tube of the X-ray exposure part 5 from the high voltage generator 9. Consequently, X-rays are exposed from the X-ray exposure part 5 towards the imaging region of the object O including the multiple phantoms P. Then, the X-rays which have transmitted the object O are detected by the X-ray detector 6.

Then, X-ray detection signals are output from the X-ray detector 6 to the medical image processing apparatus 15 through the A/D converter 14. Thereby, the digitized X-ray image data are acquired in the X-ray image acquisition part 16 of the medical image processing apparatus 15.

Since the contrast agent has been injected into the object O during the imaging period, the X-ray image data are X-ray contrast image data. Therefore, the X-ray contrast image data in which blood vessels have been depicted blackly are generated. The multiple phantoms P are also depicted in the X-ray contrast image data. Since the respective phantoms P simulate different concentrations of the contrast agent, the respective phantoms P are depicted with different densities.

Next, in Step S3, the correction function determination part 17A automatically detects the phantoms P from the X-ray contrast image data. The automatic detection of the phantoms P can be performed by image recognition, such as contour definition processing and template matching based on known form information of the phantoms P, based on the pixel values of the X-ray contrast image data. Therefore, when the forms of phantoms P are spherical, the phantoms P can automatically be recognized by pattern matching between a circular region and each of 2D regions extracted by threshold value processing of the pixel values of the X-ray contrast image data.

Next, in Step S4, the correction function determination part 17A measures the maximum value of the pixel values of each recognized phantom P. When the phantoms P are spherical, the pixel value at the center position of each phantom P shows the maximum value.

Note that, pixel values may be measured at multiple positions inside the 2D region occupied by each phantom P so that the pixel value at the center of the 2D region occupied by each phantom P can be obtained with high accuracy by interpolation processing based on the pixel values at the multiple positions.

Thereby, the maximum values of the pixel values of the multiple phantoms P are acquired as their representative values. The acquired pixel values of the multiple phantoms P are image signal values corresponding to the concentrations of the contrast agent respectively simulated by the phantoms P. In other words, the respective X-ray absorption factors of the phantoms P can be measured as the image signal values of the X-ray contrast image data.

Next, in Step S5, the correction function determination part 17A determines a nonlinear correction function or nonlinear correction functions based on the image signal values of the multiple phantoms P. For a specific example, a fourth order function, as shown by expression (1), for estimating the true values of the concentrations of the contrast agent is obtained based on the pixel values of the X-ray contrast image data. The coefficients of the correction function or the correction functions can be obtained by solving simultaneous equations, whose parameters are the pixel values of the phantoms P and the X-ray absorption coefficients, as shown by expression (2-1), expression (2-2), expression (2-3), expression (2-4), and expression (2-5).

Note that, the imaging region of the X-ray contrast image data may be divided into multiple regions and a correction function may be determined for each region. In that case, the phantom set composed of the multiple phantoms P is moved as illustrated in FIG. 14, and multiple frames of X-ray contrast image data are acquired. Alternatively, the phantom sets each composed of the multiple phantoms P are arranged at multiple positions as illustrated in FIG. 15, and at least one frame of X-ray contrast image data are acquired.

Moreover, when time series X-ray contrast image data are acquired as moving image data, a correction function or correction functions may be obtained for each time phase. In that case, correction functions can also be determined with dividing the imaging region into multiple regions. In this case, multiple correction functions corresponding to multiple time phases and multiple regions are determined.

Next, in Step S6, the image correction part 17B corrects all the pixel values of the X-ray contrast image data using the correction function or the correction functions. As a result, pixel values, whose variation component parts in signal values due to the factors, such as SIDs, influencing the image signal values have been corrected, are obtained as concentrations of the contrast agent at all the pixel positions. Then, X-ray contrast image data, whose pixel values are the concentrations of the contrast agent after the correction or the values corresponding to the concentrations of the contrast agent after the correction, can be used as a display target.

Next, in Step S7, X-ray contrast images after the correction are displayed. Specifically, the corrected values, by the correction function or the correction functions, or values corresponding to the corrected values, such as proportional values or logarithmic values of the corrected values, are given from the image correction part 17B to the display processing part 17E. Then, the display processing part 17E performs necessary display processing of the 2D X-ray contrast image data, whose pixel values are the corrected values or the values corresponding to the corrected values, and outputs the processed 2D X-ray contrast image data to the display unit 13. Thereby, the X-ray contrast images, in which the concentrations of the contrast agent are quantitatively indicated with brightness, are displayed on the display unit 13.

Note that, the X-ray absorption factors of the phantoms P may be calibrated based on the information, which indicates a relation between true values of concentrations of a contrast agent and image signal values, stored in the concentration-pixel value conversion information storing part 17D, prior to the X-ray contrast study. The information which indicates the relation between the true values of the concentrations of the contrast agent and the image signal values can be obtained in advance, by the concentration correction information acquisition part 17C, based on image signal values, corresponding to predetermined concentrations of the contrast agent, actually observed by X-ray imaging of the contrast agent having the predetermined concentrations.

That is, the X-ray diagnostic apparatus 1 mentioned above is to image multiple phantoms P, which simulate different concentrations of a contrast agent, together with an object O as a target of X-ray contrast imaging, and to calibrate pixel values of X-ray contrast image data based on image signal values of the multiple phantoms P. Moreover, the medical image processing apparatus 15 is to determine a correction function or correction functions, for obtaining quantitative concentration values of a contrast agent based on image signal values of X-ray contrast image data, based on image signal values of the phantoms P, in order to calibrate the X-ray contrast image data. Meanwhile, a phantom set composed of multiple phantoms P and an instrument for setting the phantoms P is to allow obtaining a correction function or correction functions for converting image signal values of X-ray contrast image data into quantitative concentration values of a contrast agent when the phantom set has been imaged together with an object O by X-ray contrast imaging.

Therefore, according to the X-ray diagnostic apparatus 1 and the medical image processing apparatus 15, quantification in concentrations of a contrast agent can be attained by correcting image signal values of X-ray contrast image data extremely simply.

Particularly, it is very difficult in the X-ray diagnostic apparatus 1 to estimate a dose of scattered rays, beam hardening, and the like, causing variations in image signal values, with sufficient accuracy, unlike an X-ray CT (computed tomography) apparatus. This is because a position of an object O relative to the imaging system 2 may be changed during imaging, in addition to the reason that original data acquired by the X-ray diagnostic apparatus 1 are 2D image data. For example, a dose of scattered rays entering the X-ray detector 6 changes by a non-negligible amount even when the bed 8 has moved by just 10 cm.

On the contrary, in the X-ray diagnostic apparatus 1 and the medical image processing apparatus 15, image signal values at respective pixel positions are corrected using image signal values of phantoms P depicted together with an object O in X-ray contrast image data to be acquired. That is, errors included in X-ray contrast image data are corrected based on image signal values of phantoms P acquired under same imaging conditions as imaging conditions of the X-ray contrast image data and having similar errors. Therefore, quantitative concentrations of a contrast agent can be obtained with a favorable accuracy, without preparing a huge correction table corresponding to imaging conditions, such as tube voltages and SIDs, having many variations.

Moreover, even when imaging conditions, such as a tube voltage, a tube current, a pulse width of a tube current and/or a position of the bed 8, are changed during X-ray imaging, or when body thicknesses of an object O change due to breathing, influence due to the change can be corrected. For example, even when a tube voltage applied to the X-ray tube temporally changes between frames, variations in image signal values due to the change of the tube voltage can be corrected with favorable accuracy. Similarly, even when a tube current and/or a pulse width changes between frames, variations in image signal values due to the change of the tube current and/or the pulse width can be corrected with favorable accuracy.

Moreover, in a case that image signal values are corrected by a correction table or a correction function prepared before imaging, it was impractical to correct influences due to changes in a position of the bed 8 and changes in body thicknesses of an object O by breathing. However, using image signal values of phantoms P in X-ray contrast image data makes it possible to correct the influences accurately. Furthermore, even in a case that a contrast agent has accumulated inside the body of an object O by administration of the contrast agent in a short time over elimination through the kidney, influence of the accumulated contrast agent can be corrected without a special correction.

(Second Embodiment)

Figure 18:
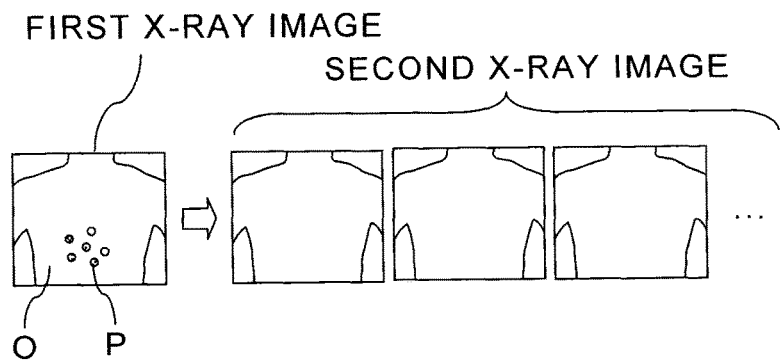
FIG. 18 is a view for explaining functions of an X-ray diagnostic apparatus and a medical image processing apparatus according to the second embodiment of the present invention.

FIG. 18 is a view for explaining functions of an X-ray diagnostic apparatus and a medical image processing apparatus according to the second embodiment of the present invention.

The X-ray diagnostic apparatus and the medical image processing apparatus in the second embodiment are different from the X-ray diagnostic apparatus 1 and medical image processing apparatus 15 in the first embodiment in the point that the image correction part is configured to be able to correct not only X-ray contrast image data, of an object including phantoms, used in order to obtain a correction function but other X-ray image data, using the correction function. The other configurations and actions of the X-ray diagnostic apparatus and the medical image processing apparatus in the second embodiment do not differ from those of the X-ray diagnostic apparatus 1 and medical image processing apparatus 15 in the first embodiment substantially. Therefore, only functions of the image correction part will be described with reference to a drawing.

The data processing part in the second embodiment is configured to generate corrected X-ray contrast image data of an object by correcting X-ray image data other than X-ray contrast image data, using a nonlinear function or nonlinear functions obtained based on pixel values, corresponding to multiple phantoms, of the X-ray contrast image data. Therefore, the imaging system and the X-ray image acquisition part acquire the first X-ray image data of an object with multiple phantoms and the second X-ray image data of the object without the multiple phantoms, as shown in FIG. 18. Then, the correction function determination part obtains a nonlinear function or nonlinear functions, as a correction function or correction functions, based on the first X-ray image data. Meanwhile, the image correction part can generate the corrected X-ray contrast image data of the object by correcting not only the first X-ray image data but also the second X-ray image data using the nonlinear function or the nonlinear functions.

Note that, it is realistic to acquire the second X-ray image data in imaging positions same as those of the first X-ray image data. Specifically, in a case that X-ray image data are acquired repeatedly with fixing the imaging system and imaging positions to a same object, changes of imaging conditions can be ignored. Therefore, the phantoms may be removed when X-ray image data corresponding to a desired frame latter than the first frame are acquired.

For a specific example, there is a case that mask image data for subtraction processing are acquired as the first X-ray image data and subsequently time series multiple frames of the second X-ray image data are continuously acquired as live image data so that subtraction image data between the first X-ray image data and each frame of the second X-ray image data can be generated. Typically, the interval between the acquisition of the mask image data and the acquisition of the live image data is about one second. Accordingly, phantoms can be imaged when the mask image data are acquired while the phantoms can be removed when the live image data are acquired.

Moreover, multiple frames of X-ray image data are occasionally acquired after an interval of about 10 minutes, depending on imaging purposes. Even in such a case, phantoms can be removed in the imaging interval. Note that, so long as there is no relative change such as a motion of an imaging part or a movement of the imaging system, the phantoms can be excluded before an acquisition of X-ray image data corresponding to an arbitrary frame after the first frame, instead of the imaging interval.

As a matter of course, correction functions may be obtained with dividing an imaging region, similarly to the first embodiment. Moreover, when multiple frames of the first X-ray image data of an object including multiple phantoms are acquired, the frames of the first X-ray image data may be acquired with changing the positions of the phantoms.

According to the X-ray diagnostic apparatus and the medical image processing apparatus in the second embodiment as mentioned above, the effect that regions where observation becomes difficult due to placing phantoms can be minimized can be attained in addition to the effects similar to those of the first embodiment.

(Other Embodiments)

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
a computer configured to:
obtain X-ray image data of an object including not less than three phantoms whose X-ray absorption factors are different from each other and whose forms are spherical, the phantoms simulating different concentrations of a contrast agent, the phantoms being used for a calibration of pixel values; and
generate corrected X-ray image data of the object by correcting the obtained X-ray image data, the obtained X-ray image data being corrected using a nonlinear function obtained based on pixel values of the obtained X-ray image data, the pixel values of the obtained X-ray image data corresponding to the phantoms,
wherein said computer is configured to obtain a nonlinear function whose influence of an error in at least one of the X-ray absorption factors of the phantoms has been corrected, based on information indicating a relation between previously obtained concentrations of a contrast agent and pixel values of X-ray image data.

2. A medical image processing apparatus of claim 1, wherein said computer is configured to:

obtain first X-ray image data of the object including the phantoms and second X-ray image data of the object without the phantoms; and generate the corrected X-ray image data of the object by correcting the second X-ray image data using the nonlinear function.

3. A medical image processing apparatus of claim 1, wherein said computer is configured to obtain the nonlinear function based on pixel values corresponding to X-ray absorption factors distributing at unequal intervals.

4. A medical image processing apparatus of claim 1, wherein said computer is configured to obtain a cubic equation, a quartic equation or a quintic equation as the nonlinear function.

5. A medical image processing apparatus of claim 1, wherein said computer is configured to obtain nonlinear functions corresponding to regions different from each other and correct the different regions respectively using the nonlinear functions, the nonlinear functions being obtained based on frames of X-ray image data obtained in states where a phantom set consisting of the phantoms has been arranged in the different regions.

6. A medical image processing apparatus of claim 1, wherein said computer is configured to obtain nonlinear functions corresponding to regions different from each other and correct the different regions respectively using the nonlinear functions, the nonlinear functions being obtained based on one frame of X-ray image data obtained in a state where a phantom set consisting of the phantoms has been arranged in each of the different regions.

7. A medical image processing apparatus of claim 2, wherein said computer is configured to obtain the second X-ray image data at a same imaging position as an imaging position of the first X-ray image data.

8. An X-ray diagnostic apparatus comprising:

an X-ray tube and an X-ray detector configured to acquire X-ray image data of an object including not less than three phantoms whose X-ray absorption factors are different from each other and whose forms are spherical, the phantoms simulating different concentrations of a contrast agent, the phantoms being used for a calibration of pixel values; and a computer configured to generate corrected X-ray image data of the object by correcting the acquired X-ray image data, the acquired X-ray image data being corrected using a nonlinear function obtained based on pixel values of the acquired X-ray image data, the pixel values of the acquired X-ray image data corresponding to the phantoms, wherein said computer is configured to obtain a nonlinear function whose influence of an error in at least one of the X-ray absorption factors of the phantoms has been corrected, based on information indicating a relation between previously obtained concentrations of a contrast agent and pixel values of X-ray image data.

9. A medical image processing method comprising:

obtaining X-ray image data of an object including not less than three phantoms whose X-ray absorption factors are different from each other and whose forms are spherical, the phantoms simulating different concentrations of a contrast agent, the phantoms being used for a calibration of pixel values;

generating corrected X-ray image data of the object by correcting the obtained X-ray image data, the obtained X-ray image data being corrected using a nonlinear function obtained based on pixel values of the obtained X-ray image data, the pixel values of the obtained X-ray image data corresponding to the phantoms; and obtaining a nonlinear function whose influence of an error in at least one of the X-ray absorption factors of the phantoms has been corrected, based on information indicating a relation between previously obtained concentrations of a contrast agent and pixel values of X-ray image data.

10. A medical image processing apparatus of claim 1, wherein said computer is configured to obtain the nonlinear function based on pixel values corresponding to center portions of the phantoms.

11. A medical image processing apparatus of claim 10, wherein the phantoms are automatically recognized by pattern matching, and pixel values at center portions of the recognized phantoms are measured.

12. A medical image processing apparatus of claim 10, wherein the pixel values corresponding to the center portions of the phantoms are obtained by measuring a maximum value of pixel values corresponding to each of the phantoms.

* * * * *